(12) United States Patent
Rose

(10) Patent No.: US 7,541,493 B2
(45) Date of Patent: Jun. 2, 2009

(54) MODAFINIL SYNTHESIS PROCESS

(75) Inventor: Sébastien Rose, Arsy (FR)

(73) Assignee: Cephalon France, Maisons Alfort (FR)

( * ) Notice: Subject to any disclaimer, the term of this patent is extended or adjusted under 35 U.S.C. 154(b) by 422 days.

(21) Appl. No.: 10/557,072

(22) PCT Filed: May 5, 2004

(86) PCT No.: PCT/IB2004/001409

§ 371 (c)(1),
(2), (4) Date: Apr. 18, 2006

(87) PCT Pub. No.: WO2004/101503

PCT Pub. Date: Nov. 25, 2004

(65) Prior Publication Data

US 2007/0015836 A1 Jan. 18, 2007

(30) Foreign Application Priority Data

May 16, 2003 (EP) .................................. 03291152

(51) Int. Cl.
*C07C 231/24* (2006.01)
*C07C 231/02* (2006.01)
*C07C 315/04* (2006.01)
*C07C 315/06* (2006.01)

(52) U.S. Cl. ....................................... 564/134; 564/162

(58) Field of Classification Search ................. 564/134, 564/162
See application file for complete search history.

(56) References Cited

U.S. PATENT DOCUMENTS

| 4,177,290 A | 12/1979 | Lafon | 424/324 |
| 4,927,855 A | 5/1990 | Lafon | 514/618 |
| 5,618,845 A | 4/1997 | Grebow et al. | 514/618 |
| 5,719,168 A * | 2/1998 | Laurent | 514/357 |

FOREIGN PATENT DOCUMENTS

| WO | WO 96/11001 | 4/1996 |
| WO | WO02/10125 A1 | 2/2002 |
| WO | WO2004/014846 A1 | 2/2004 |

OTHER PUBLICATIONS

U.S. Appl. No. 10/539,918, filed Feb. 17, 2006, Neckebrock et al.
U.S. Appl. No. 10/541,527, filed Oct. 27, 2005, Rose et al.
U.S. Appl. No. 10/943,360, filed Sep. 17, 2004, Rebiere.
U.S. Appl. No. 11/082,530, filed Mar. 17, 2005, Rebiere.
U.S. Appl. No. 11/224,250, filed Sep. 12, 2005, Hauck.
U.S. Appl. No. 11/374,227, filed Mar. 13, 2006, Prat.

* cited by examiner

*Primary Examiner*—Peter G O'Sullivan

(57) ABSTRACT

The invention relates to a process for preparing modafinil having a defined granulometry which comprises the steps of: a) preparing a solution of DMSAM; b) contacting the solution obtained with NH3 at a predetermined temperature and a predetermined stirring; and c) isolating the modafinil formed, wherein said temperature and said stirring are predetermined in order to obtain said defined granulometry.

31 Claims, No Drawings

MODAFINIL SYNTHESIS PROCESS

CROSS-REFERENCE TO RELATED APPLICATIONS

This application represent entry into the U.S. national phase of International Application No. PCT/IB2004/001409, filed May 5, 2004, which in turn claims priority of European Application No. EP 03 291 152.1, filed May 16, 2003.

FIELD OF THE INVENTION

The present invention is directed to a process for preparing modafinil having a defined granulometry.

BACKGROUND OF THE INVENTION

Modafinil ($C_{15}H_{15}NO_2S$) of formula I, 2-(benzhydrylsulphinyl)-acetamide, is a synthetic acetamide derivative possessing wakefulness-promoting activity, whose structure has been described in U.S. Pat. No. 4,177,290 and whose racemic form has received the approval of the registration authorities for use in the treatment of narcolepsy.

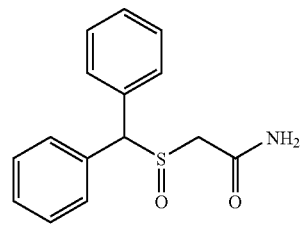
(I)

Example 1 (scheme 1) of U.S. Pat. No. 4,177,290 (Lafon) describes a process for preparing modafinil which comprises reacting benzhydrylthioacetic acid with thionyl chloride in a first step. The acid chloride obtained is then reacted with ammonia to give the corresponding acetamide. Finally, in a last step, the sulphur atom of this intermediate is oxidized in the presence of hydroperoxide in acetic acid to give modafinil.

Scheme 1

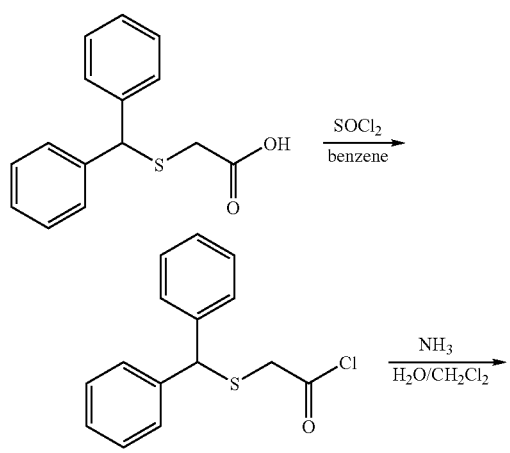

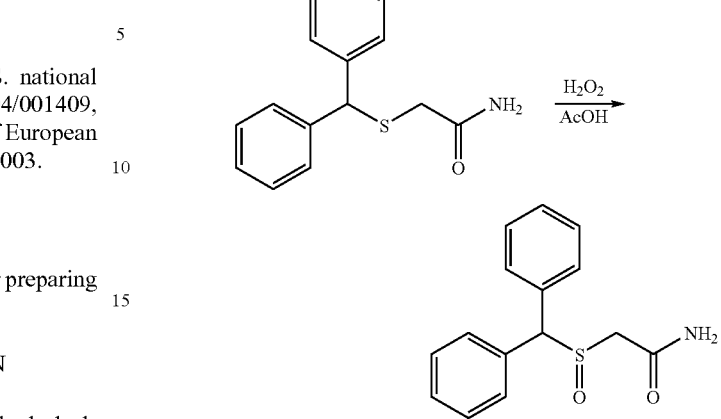

The drawback of this process is that the step of oxidizing the sulphur of the 2-[(diphenylmethyl)thio]acetamide intermediate in the presence of hydrogen peroxide is difficult to control and may lead to the formation of a sulphone by-product (II) which is difficult to separate from the modafinil.

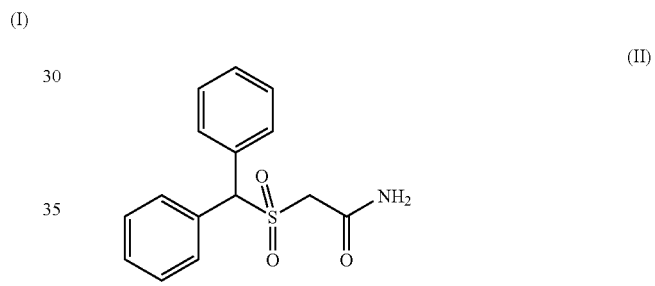
(II)

Patent application WO 02/10125 (TEVA) describes a process for preparing modafinil which takes the same kind of approach. In this application, however, the step of oxidizing the sulphur of the 2-[(diphenylmethyl)thio]acetamide is carried out using hydrogen peroxide in the presence of a mineral acid such as $H_2SO_4$, $HClO_4$ or $H_3PO_4$ and a linear, branched or cyclic alcohol or a phase transfer catalyst, optionally in an inert organic solvent.

According to the authors these conditions are particularly suitable for the oxidation of sterically hindered sulphides such as modafinil and allow the oxidation step to be controlled and in particular the formation of the sulphone by-product (II) to be avoided.

Example 1a of U.S. Pat. No. 4,177,290 (scheme 2) proposes a quite different approach for the industrial-scale preparation of modafinil. Thus the oxidation of the sulphur atom of benzhydrylthioacetic acid in the presence of hydrogen peroxide takes place in the first step. The intermediate obtained is then converted to the methyl ester, i.e. methyl diphenylmethylsulphinyl-acetate (DMSAM), by reaction with dimethyl sulphate. Finally, after gaseous ammonia has been bubbled into a methanolic solution of DMSAM for one hour, the reaction mixture is left in contact for four hours. The modafinil thus obtained is isolated and recrystallized in two stages.

Scheme 2

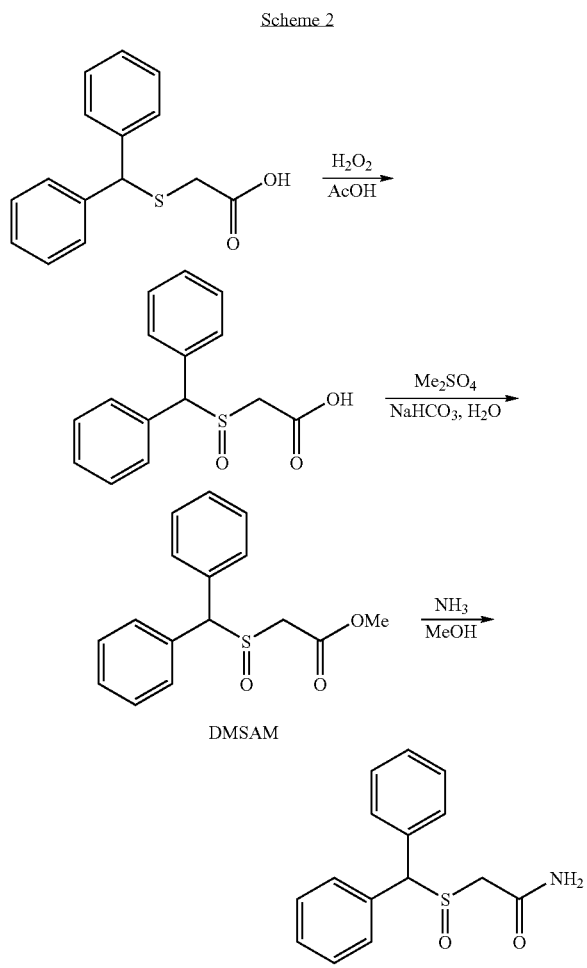

This preparation process, however, has drawbacks. In particular it involves a plurality of steps of recrystallization of the modafinil obtained, and presents a mediocre yield.

U.S. Pat. No. 4,927,855 (Lafon) describes the synthesis of levorotary modafinil by reaction of a 0.3 mol·L$^{-1}$ solution of (−)-DMSAM with ammonia at ambient temperature. Following recrystallization, however, the levorotary modafinil is obtained with a modest yield.

Studies have shown, moreover, that the particle size of the modafinil has a great influence on the pharmacological efficacy of the compound.

Thus, according to application WO 96/11001 (Cephalon), small modafinil particles induce an increase in the pharmacological efficacy of modafinil, probably by promoting its absorption as compared with larger particles.

In that context the said application describes pharmaceutical compositions comprising a homogeneous mixture of modafinil particles of defined granulometry (mean (2 to 19 μm), median (2 to 60 μm)). These particles are obtained after grinding of the modafinil prepared by the conventional methods, in order to reduce the size of the particles or aggregates, followed by screening of the resultant particles to give a defined particle size distribution.

Furthermore, racemic modafinil can be obtained in different polymorphic forms or in the form of a mixture of these polymorphs, depending on the operating conditions employed (WO 02/10125 (TEVA)).

Since the various polymorphs of modafinil may present very different physical, pharmaceutical, physiological and biological properties it is important to have available a preparation process which allows one single polymorph to be obtained with simplicity and rapidity.

SUMMARY OF THE INVENTION

One of the aims of the present invention is to provide a process which allows modafinil to be obtained directly in the form of particles of defined granulometry.

Another aim of the present invention is to furnish a process which allows modafinil to be obtained in a single polymorph. This process makes it possible in particular to obtain selectively different polymorphs of modafinil.

A further aim of the invention is to furnish a process which allows modafinil to be obtained directly, without a subsequent purification step, in a purity of more than 99.5% and with high yields.

DETAILED DESCRIPTION OF THE INVENTION

The existence has now been found of two polymorphs in the process of crystallization of racemic modafinil. These two polymorphs, while being of identical chemical composition, possess different crystalline network energies and, consequently, different solubilities in a given crystallization solvent.

More specifically it has been shown that one of the polymorphs has a high nucleation frequency and therefore crystallizes first, for reasons of kinetics. Under equilibrium conditions this kinetic polymorph tends to disappear to the benefit of a second polymorph which is thermodynamically more stable.

It has also been found that the polymorphic transformation of the kinetic form to the thermodynamic form is accompanied by a change in the granulometry of the modafinil.

The kinetic and thermodynamic forms of racemic modafinil will be referred to hereinbelow as forms III and I respectively. These forms are as identified in WO 2004/014846. It is form I which in fact corresponds to the modafinil polymorph which has received the approval of the registration authorities.

In the course of studies aimed at optimizing the modafinil manufacturing process, the inventors discovered operating conditions which allow both the granulometry of the end product and its polymorphism to be controlled and hence obviate the subsequent processing steps of the synthesized modafinil.

Thus, by mastering the operating parameters employed during the process the inventors have shown that it is possible to obtain modafinil particles of well-defined polymorphism and size.

Specifically, there are three operating parameters which allow the particle size distribution of the end product to be controlled, and these are:
the concentration of the DMSAM used as reactant;
the reaction temperature; and
the stirring speed.

In practice, one of the three parameters, for example the concentration of the DMSAM solution, is fixed in a first phase and the two other parameters, i.e. the temperature and the stirring speed, are predetermined as a function of the desired granulometry of the modafinil.

The particle size distribution in the sense of the present invention is defined by the granulometric mean, median, mode, and profile.

All particle size measurement (granulometry) techniques operate on a large number of particles which make up what is called a "population". The population is divided into size classes (on the abscissa) and their relative proportions are expressed as a frequency (on the coordinate).

The term "granulometric mean" in the sense of the present description denotes the sum of the measured sizes of the measurable modafinil particle population divided by the total number of particles measured. For example, for five measurable particles found by measurement to have diameters respectively of 20 µm, 23 µm, 20 µm, 35 µm and 20 µm the mean diameter would be 23.6 µm.

The "granulometric mode" denotes the most frequent particle size value in the distribution. For example, for the five particles listed above, the mode would be 20 µm. A distribution may have a single mode or several modes. Accordingly, a distribution which has a single granulometric mode is monomodal. A distribution possessing two granulometric modes is said to be bimodal.

The "granulometric median" in the sense of the present description corresponds to the equivalent diameter for which the cumulative distribution value is 50%. In other words this signifies that 50% of the measurable particle population measured have a particle diameter lower than the median diameter defined and that approximately 50% of the measurable particle population measured have a diameter greater than the median diameter defined. For example, for the five particles listed above, the median diameter would be 20 µm.

In the sense of the present description the "granulometric profile" relates to the distribution of the particle sizes as a function of their relative proportion and allows the number of populations of particles to be defined.

The median measurement is generally considered as having greater importance compared to the mode or mean values in that the median value provides an indication of the distribution of the particles measured in a given population.

In general terms, the inventors have shown that, for a given concentration and at constant temperature, a high stirring speed promotes the formation of two particle populations and tends to lower the granulometric median.

Conversely, for a given concentration and a constant stirring speed, a high reaction temperature, greater in particular than 24° C., promotes a bimodal granulometric profile and brings about the growth of the population of particles which are greater in size and, consequently, an increase in the value of the granulometric median. A lower reaction temperature (T<24° C.), on the other hand, tends to promote a more uniform (monomodal) granulometric profile and a higher mode, which may be accompanied by an increase in the granulometric median.

The inventors have in fact demonstrated that mastery of the temperature and stirring speed in the reaction of DMSAM with ammonia allows the polymorphic transformation, in this case the conversion of form III to form I, and the granulometric profile of the modafinil, to be controlled.

The object of the present invention is therefore to provide a process for preparing modafinil particles of defined and controlled granulometry and polymorphism, starting from DMSAM.

As used herein, the term "having a defined granulometry", when used in reference to modafinil, is understood as an homogeneous particle size distribution. While not necessarily a limitation but rather an indicator of the consistency of the population measured, the ratio of median:mean:mode would ideally be 1:1:1; however, a ratio of median to mean of 1:3 to 1:0.3 is acceptable, and a ratio of median to mode of 1:3 to 1:0.3 is acceptable.

More specifically, the invention is directed to a process for preparing modafinil which comprises the steps of:

a) preparing a solution of DMSAM in a solvent;
b) contacting the solution obtained with $NH_3$ at a predetermined temperature and under a predetermined stirring; and
c) isolating the modafinil formed, wherein said temperature and said stirring are predetermined in order to obtain said defined granulometry.

The process of the invention is directed preferably to the preparation of racemic modafinil from racemic DMSAM.

The concentration of the DMSAM solution exerts an influence over the granulometry of the modafinil obtained by this process.

Generally speaking, for a given temperature and stirring speed, the greater the dilution of the medium, the higher the granulometric median of the modafinil obtained. Conversely, the greater the concentration of the medium, the more the granulometric median will tend to reduce.

In practice, the concentration of the DMSAM solution is fixed at a level close to the saturation concentration of DMSAM in the solvent in question but not greater than that concentration, so as to prevent the reaction medium solidifying.

In this context, the solution of DMSAM has a concentration of DMSAM of between 1 and 1.25 mol $L^{-1}$.

The reaction of the process claimed herein is carried out in a suitable solvent which may be readily selected by one skilled in the art, the suitable solvent generally being any solvent which is substantially non reactive with the starting materials, the intermediates and products at the temperature and pressure at which the reaction is carried out.

The suitable solvent preferably better solubilises the reactants, DMSAM and $NH_3$, than modafinil.

Such solvents include notably polar protic solvents.

Suitable polar protic solvents include alcohols such as methanol, ethanol, propanol, butanol, i-butyl alcohol, t-butyl alcohol, methoxyethanol, ethoxyethanol, pentanol, neopentyl alcohol, t-pentyl alcohol, cyclohexanol, ethylene glycol, propylene glycol, benzyl alcohol, phenol and glycerol, methanol being preferred.

"$NH_3$", as used herein, may refer to gaseous or liquid ammonia, ammonium hydroxide and, by extension, to any compound capable of generating ammonia in the reaction mixture, gazeous ammonia being preferred.

By virtue of the adjustment of the parameters of temperature and stirring speed in step b) the process of the invention makes it possible, for a fixed concentration, to obtain batches of modafinil of specific granulometry whose respective medians may vary between 1 µm et 1 mm, in particular between 1 and 900 µm, 1 and 700 µm, 1 and 500 µm, 1 and 300 µm, 1 and 200 µm, and preferably between 2 and 60 µm, more preferably between 15 and 45 µm.

In practice, given the desired granulometry, the temperature can be set prior to the stirring speed and the stirring speed adapted accordingly, or conversely. Thus, temperature and stirring speed both determine the granulometry obtained.

The temperature may vary from room temperature up to the higher temperature at which the formation of modafinil particles may still be observed in the solvent. In that respect, the inventors have evidenced that, in the given conditions of the reaction, there is a limit temperature above which the solubility of modafinil becomes too high for allowing particles formation. It is understood that this limit depends notably on the nature of the solvent.

The temperature is chosen sufficiently high to promote the kinetic of the reaction of DMSAM with $NH_3$, and not too high so that the modafinil has a poor solubility in the solvent.

The temperature in step b) is preferably maintained between 15 and 65° C., more preferably between 20° and 30° C., and most preferably between 23° and 27° C.

It should be noted that the stirring speed appropriate to the realization of the invention may vary in particular as a function of the geometry and size of the reactor and of the type of stirring element.

It will therefore be appropriate for the person skilled in the art to determine the stirring speed as a function of the equipment employed (particularly as a function of the limits of the apparatus and the scale of operation) and of the desired granulometry, taking into account the indications provided by the present invention.

In one particular embodiment, the stirring speed in step b) makes it possible to obtain particles of modafinil form I with a granulometric median ranging from 2 to 60 μm, more preferably from 15 to 45 μm.

By way of example, in order to obtain batches of modafinil with a granulometric median of between 2 and 60 μm, for a DMSAM solution close to saturation and for a temperature of 25° C. with a reactor of type AE 100 (De Dietrich) with a capacity of 100 liters, equipped with a three-branched stirring element of the impeller type, preference will be given to a stirring speed of between 125 and 175 rpm, more preferably 150 rpm.

The impeller stirrer here denotes a stirring element having three branches which is characterized by the following dimensionless parameters in turbulent regime: power number $N_p=0.5$; flow number $N_q=0.29$; Nusselt constant $A=0.36$.

In another example, with a reactor of type Simular (HEL: Hazard Evaluation Laboratory) having a capacity of one liter and for a DMSAM solution close to saturation and for a temperature of 25° C., it is preferred to operate with a stirring speed ranging from 300 to 400 rpm, more preferably 350 rpm, to give batches of modafinil particles whose granulometric median is between 2 and 60 μm.

The solution of DMSAM is contacted with 3 to 6, more preferably 3.2 to 5, and most preferably close to 3.6 molar equivalent of $NH_3$.

Generally, the process is carried out with gaseous ammonia. This can be introduced in particular using conventional devices which allow the ammonia to be bubbled into the reaction medium. It has additionally been noted that, in the absence of mechanical stirring, bubbling alone does not have any effect on the granulometry of the modafinil.

The $NH_3$ is introduced into the solution in step b) over a time sufficient to obtain a complete dissolution of $NH_3$, preferably of between 2 h and 6 h, more preferably of between 3 h and 4.5 h.

As used herein, a "complete dissolution", when used in reference to $NH_3$, means a dissolution of 95% to 100% of the amount of ammonia gas introduced, more preferably superior than 98% and most preferably superior than 99%.

Incomplete dissolution of the ammonia in the reaction medium is liable to have an adverse effect on the yield of the reaction and on the purity of the product obtained.

Modafinil is then obtained in form III, in particular with a monomodal granulometric profile. The modafinil may optionally be isolated in this polymorphic form by proceeding to step c) directly.

The process of the invention therefore allows the preparation of modafinil form III, monomodal in particular.

In one preferred embodiment, following the introduction of the $NH_3$, the solution in step b) is contacted at the predetermined temperature and at the predetermined stirring speed, for a time sufficient to allow the polymorphic transformation from form III to form I.

It is preferred to employ a contact time of between 8 h and 12 h.

The median is then lower in value than that obtained at the end of introduction of $NH_3$.

The process of the invention therefore allows the preparation of modafinil form I.

In a preferred variant, the solution obtained after step b) is further maintained at a temperature lower than the temperature of step b), preferably between −20° C. and 0° C., for a period sufficient to obtain complete crystallization of modafinil, and preferably of from 1 h to 4 h.

As used herein, a "complete crystallization" means when used in reference to modafinil, a crystallization of 85% to 100% of the amount of modafinil formed in solution, more preferably superior than 90% and most preferably superior than 92%.

The modafinil particles are advantageously isolated from the solution by filtration in step c) and then are generally subjected to a drying step, preferably at a temperature of between 40 and 50° C.

This process may also be implemented in the presence of water.

Thus, in one particular embodiment, the polar solvent in step a) of the process comprises water, preferably from 5 to 20% by volume of water.

In this context, the $NH_3$ is introduced into the solution over a time preferably of between 4 h and 5 h in step b).

In this particular variant, the DMSAM solution is preferably contacted with 5 to 5.5 molar equivalent of $NH_3$.

Specifically, the temperature and the stirring speed of the reaction medium in step b) have a much more sensitive influence on the granulometric median in the process with water.

Advantageously, the process of the invention allows the granulometric profile of the modafinil obtained to be controlled by way of a mastered polymorphic transformation.

Interestingly, the process of the invention makes it possible to obtain a single polymorph without the need to carry out a recrystallization following step c).

Thus, the form III obtained as an intermediate at the outcome of step b) may either be isolated directly or maintained in contact with ammonia for a period sufficient to give form I, which is then isolated.

Advantageously, the process of the invention makes it possible to obtain, without any subsequent step of either grinding or screening, particles having controlled granulometric medians, depending on the operating conditions employed.

It is possible, of course, to carry out a subsequent grinding step in order to reduce still further the size of the particles obtained by the process of the invention and thus to obtain nanometer-sized particles.

In particular, the process allows the simple and straightforward preparation of batches of particles of modafinil form I which have specific granulometric medians, preferably of between 2 and 60 μm, in particular between 15 and 45 μm.

In one preferred embodiment, the predetermined stirring and temperature are chosen such that particles of modafinil of form I of which at least 50% have a diameter less than 45 μm, at least 80% have a diameter less than 110 μm and at least 95% have a diameter less than 220 μm, are isolated in step c).

The process of the invention, illustrated in specific fashion in the foregoing text by the preparation of racemic modafinil, may also be applied to the preparation of levorotary modafinil. The latter is described in particular in U.S. Pat. No. 4,927,855, and has been identified as displaying the absolute configuration R. In this context, the DMSAM is employed in step a) in its levorotary enantiomeric form, which may be prepared in particular in accordance with U.S. Pat. No. 4,927,855.

The process of the invention may also be applied to the preparation of dextrorotary modafinil. In this context, the DMSAM is employed in step a) in its dextrorotary enantiomeric form, which may be prepared in particular in accordance with U.S. Pat. No. 4,927,855.

The invention is also directed to modafinil obtainable by this process, which has been showed to display characteristic and reproducible particle size distribution and impurity profile.

EXAMPLES

Apparatus and Methods

Laser diffraction granulometer, Beckman-Coulter model LS 100:

0.4 μm to 800 μm in one analysis 72 particle size classes 126 detectors used dry I. Modafinil Synthesis Process with Water A. 1-Liter Scale

Example 1

1-Liter Scale Procedure

A 1-liter reactor of type SIMULAR (Hazard Evaluation Laboratory, HEL) equipped with an impeller stirrer and a gas introduction tube was charged with 150 g of DMSAM, 450 ml of methanol and 33 mL of water. The suspension was stirred at 100 rpm and 20° C. for 10 min and then heated to 35° C. to dissolve the solids. The solution was subsequently stirred at 200 rpm for 10 min, then cooled to 25° C. and stirred at 350 rpm and at this temperature for 20 min.

46.8 g of ammonia were then introduced over 4.5 h at 25° C.

The reaction medium was left in contact for 10 h at 25° C. with stirring at 350 rpm before finally being cooled to −10° C. and then filtered over a frit of porosity 3.

The moist product was then dried under vacuum at 45° C. Yield=89%, median=34.1 μm.

Examples 2 to 5

Effect of temperature and Stirring Speed on Granulometry

Example 2

Standard (Zero-Point) Experiment and Reproducibility

Conditions of standard experiment were the same as those of example 1.

The point at which the ammonia was injected, the jacket temperature, the cooling rate and the contact time at −10° C. were maintained constant during the various experiments, since these parameters had little or no influence on controlling the granulometry of the modafinil synthesized.

A standard experiment was desired in order to obtain a final granulometric median which was situated in the range 15-45 μm and thus to constitute a zero point of comparison for the subsequent experiments.

This search then culminates in the following conditions:

reaction temperature T=25° C., stirring speed SS=350 rpm, ammonia introduction time t=4.5 h.

Under these conditions the granulometric median obtained, G, was 34 μm.

This standard experiment was then repeated in order to assess its reproducibility: that was, three experiments conducted at T=25° C. (including 2 experiments with regulation via the temperature of the mass and one experiment with regulation via the jacket temperature), SS=350 rpm, and t=4.5 h.

Identical results were obtained within a 3 μm band and with similar granulometric profiles.

| Experiment | Temperature regulation | Granulometric median G | 95% C.F. | % < 220 μm |
|---|---|---|---|---|
| H980503 | Mass | 34.14 μm | 0-171 | 98.1 |
| H980504 | Jacket | 34.09 μm | 0-174 | 98.3 |
| H980505 | Mass | 31.31 μm | 0-160 | 98.9 |

CF: Confidence interval represented.

These conditions therefore represented the standard experiment which could be used as a basis for any comparison. The reproducibility of the reaction system (apparatus+synthesis) was also assured. Furthermore, these experiments demonstrated the minor role of the choice of the control of temperature in this process: mastery of the crystallization exotherm was therefore not critical for the final granulometric result.

Example 3

Study of the Effect of Stirring Speed

This parameter was varied in order for its influence on the particle size distribution to be assessed. Two values situated on either side of the value found in the standard experiment were selected, the other parameters being kept at their standard value.

The results obtained were as follows:

| Experiment | Speed SS | Median G | Mean | 95% C.F. | % <220 μm |
|---|---|---|---|---|---|
| Standard | 350 | 33.18 | 55-60.1 | 0 to 160-174 | 98.1-98.9 |
| H980502 | 300 | 49.12 | 81.48 | 0 to 231.8 | 94.4 |
| H980601 | 400 | 28.18 | 47.5 | 0 to 140.3 | 99.4 |

CF: Confidence interval.

These results showed that the stirring speed had a considerable influence on the particle size distribution of the product obtained. The higher the speed, the lower the granulometric median. The particle size curve then showed a second, smaller population beyond 60 μm.

Conversely, a lower stirring speed promoted the formation of large particles.

Increasing the stirring speed therefore made it easier to obtain a low and uniform particle size.

Example 4

Effect of Reaction Temperature

This factor may be critical for effecting successful synthesis of modafinil and for the final granulometry, on a number of levels:
- effect on the chemical kinetics of the reaction between DMSAM and ammonia,
- effect on the nucleation kinetics of the crystals, by shifting the solubility curves and supersaturation curves of modafinil in methanol,
- effect on the growth kinetics of the crystals formed.

As before, two experiments were carried out by varying the value of this factor on either side of its standard value, while keeping all of the other parameters the same.

The results obtained were as follows:

| Experiment | Temperature T | Median G | Mean | 95% C.F. | % <220 μm |
|---|---|---|---|---|---|
| Standard | 25 | 33.18 | 55–60.1 | 0 to 160–174 | 98.1–98.9 |
| H980506 | 23 | 33.04 | 50.69 | 0 to 139.8 | 99.8 |
| H980507 | 27 | 42.64 | 69.71 | 0 to 191.4 | 97.3 |

CF: Confidence interval.

At 23° C., although the value of the median was close to that obtained at 25° C., the granulometric profile was different: the second population beyond 60 μm was more attenuated, so making the distribution more Gaussian.

Conversely, the results obtained at 27° C. featured both a higher granulometric median and a much larger second population.

Reducing the reaction temperature therefore made it easier to obtain a low and uniform particle size.

Example 5

Combination of the Effects

The above experiments showed that the increase in the stirring rate and the decrease in the reaction temperature were two favourable parameters, in isolation, for obtaining particles of low size and uniform distribution.

The combined influence of these two parameters on the final granulometry of the modafinil was studied. For this purpose a last experiment was conducted under the following conditions:
- reaction temperature T=23° C.,
- stirring speed SS=400 rpm,
- ammonia introduction time t=4.5 h.

The curve obtained showed the following characteristics:
- median=32.92 μm,
- mean=42.11 μm,
- 95% C.F.=0 to 106.6 μm,
- %<220 μm=100.

The particle size distribution was highly uniform and the median is very satisfactory.

Conclusions:

These experiments demonstrated two critical operating parameters and their effects, namely:
- the reaction temperature T: decreasing it allows a low and uniform particle size to be obtained,
- the stirring speed SS: increasing it allows a low and uniform particle size to be obtained.

These two parameters vary in isolation or combination to give batches of uniformly low, medium or high specific particle size. By way of example, batches whose median is between 2 and 60 μm, 60 and 120 μm, 120 and 200 μm, 200 and 300 μm, 300 and 500 μm, 500 and 700 μm, 700 and 900 μm can be prepared in this way.

B. 100-Liter Scale

Example 6

100-Liter Scale Procedure

A pilot-scale reactor of type AE 100 (De Dietrich) with a capacity of 100 liters, equipped with an impeller stirrer (De Dietrich) and a gas introduction pipe, was charged with 15 kg of DMSAM, 45 liters of methanol and 33 mL of water. The suspension was stirred at 100 rpm and 20° C. for 10 min and then heated to 35° C. to dissolve the solids. The solution was subsequently stirred at 150 rpm for 15 min, then cooled to 25° C. and stirred at 150 rpm at this temperature for 30 min.

4.68 kg of ammonia were then introduced over 4.5 h at 25° C.

The reaction medium was left in contact for 10 h at 25° C. with stirring at 150 rpm before finally being cooled to −10° C., and was then drained and clarified with 20 liters of ice-cold methanol.

The moist product was then dried under vacuum at 45° C. Yield=87%, median=46.6 μm.

Examples 7 to 9

Study of the Operating Parameters

Example 7

Standard Experiment (Zero Point) and Reproducibility

In order to assess the reproducibility of the process on the pilot scale, three experiments were carried out under identical conditions, which were defined as "standard" for the remainder of the study:
- T=25° C.,
- SS=150 rpm,
- t=4.5 h,
- regulation via the temperature of the mass,
- D=12 m³/h.

The results obtained were as follows:

| Experiment | Granulometric median | Number of populations | Most well-defined mode |
|---|---|---|---|
| P980907 | 46.6 μm | 2 | 27.6 μm |
| P981003 | 51.2 μm | 2 | 22.28 μm |
| P981004 | 49.9 μm | 2 | 22.28 μm |

This gave the following definition of a standard experiment, on the basis of the calculated means:

| | | | |
|---|---|---|---|
| Standard | 49.2 μm | 2 | 24 μm |

The reproducibility of the process on the pilot scale (100 L) was therefore verified, since the results obtained were homogeneous. These conditions represented the standard experiment which served as a basis for any comparison in the remainder of the study.

Example 8

Study of the Effect of Stirring Speed

In order to verify the significance of this parameter, experiments were conducted at two different stirring speeds: 100 rpm and 150 rpm (standard value). The other parameters were held at their standard value.

The results obtained were as follows:

| Experiment | Speed SS | Median G | Number of populations |
|---|---|---|---|
| Standard | 150 | 49.2 μm | 2 |
| P980906 | 100 | 119.3 μm | 2 |

The effect of this parameter on the granulometry of the end product was identical to that demonstrated at the 1-liter scale: increasing the stirring speed made it easier to obtain a lower median.

Example 9

Study of the Effect of Reaction Temperature

The reaction temperature was demonstrated to effect the results on the laboratory scale. In order to verify it on the pilot scale, three experiments were conducted by varying the value of this factor either side of its standard value, all of the other operating parameters being kept the same.

The results obtained were as follows:

| Experiment | Temperature T | Median G | Number of populations | Most well-defined mode | % <220 μm |
|---|---|---|---|---|---|
| P980908 | 23 | 48.9 | 1 | 47.2 | 99.1 |
| P981006 | 24 | 52.9 | 2 | 22.8 | 90.3 |
| Standard | 25 | 49.2 | 2 | 24 | 89.8 |
| P981001 | 26 | 70.1 | 2 | 24 | 81.5 |

These results were identical to those obtained on the laboratory scale (1 liter): increasing the reaction temperature gave rise to the growth of a second population of larger particles and, consequently, an increase in the value of the median.

Conversely, a lower reaction temperature (T<24° C.) made it possible to obtain a more uniform granulometric profile. The granulometric mode, however, was then higher, which could have consequences for the median (where there was a possibility of increase since the median and the mode merge in the case of a perfectly Gaussian profile).

In any case, in order to obtain a granulometric median in accordance with the specifications it would be necessary to raise the stirring speed to 175 rpm.

As in the preceding example, on this pilot scale, the granulometry depended on the initial definition of two parameters: temperature and stirring speed. Batches of finished product with specific and uniformly low, medium or high particle size whose mean or median was centred on a value between the limits 1 μm and 1 mm could be obtained.

Example 10

Additional Study on the Crystallization

In order to complete the study on the control of the particle size distribution of the end product and in order to gain a better understanding of the crystallization phenomenon involved in this process, samples of the reaction medium were taken during various experiments. These samples, taken either at the end of the exotherm produced by the crystallization (and indexed (EX)) or at the end of the 10 hours of contact with ammonia, isolation and drying (and indexed EP for end product), were subjected to a particle size analysis and to a crystalline analysis by X-ray scattering.

| No. | Entry | T° C. | S (rpm) | Mode (μm) | Median (μm) | Mean (μm) | Number of populations | Polymorph |
|---|---|---|---|---|---|---|---|---|
| 1 | P980907 EX | 25 | 150 | 211.6 | 143.9 | 144.4 | 1 | III |
| 2 | P980907 EP | 25 | 150 | 27.61* | 46.65 | 69.94 | 2 | I |
| 3 | P980908 EX | 23 | 150 | 170.8 | 147.7 | 138.3 | 1 | III |
| 4 | P980908 EP | 23 | 150 | 47.19* | 48.91 | 61.42 | 1 | I |
| 5 | P981001 EX | 26 | 150 | 235.6 | 222.1 | 215.4 | 1 | III |
| 6 | P981001 EP | 26 | 150 | 24* | 70.13 | 111.5 | 2 | I |
| 7 | P981002 EX | 25 | 150 | 211.6 | 193.1 | 188.8 | 1 | III |
| 8 | P981002 EP | 25 | 150 | 22.3* | 68.06 | 101.9 | 2 | I |
| 9 | P981003 EX | 25 | 150 | 262.3 | 243.1 | 233.3 | 1 | III |
| 10 | P981003 EP | 25 | 150 | 22.28* | 51.23 | 101.2 | 2 | I |
| 11 | P981004 EX | 25 | 150 | 291.9 | 255.1 | 246.0 | 1 | III |
| 12 | P981004 EP | 25 | 150 | 22.3* | 49.93 | 99.54 | 2 | I |
| 13 | P981005 EX | 25 | 150 | 190.1 | 180.3 | 176.5 | 1 | III |
| 14 | P981005 EP | 25 | 150 | 22.3* | 48.56 | 94.80 | 2 | I |
| 15 | P981006 EX | 24 | 150 | 190.1 | 178.1 | 173.3 | 1 | III |
| 16 | P981006 EP | 24 | 150 | 22.8* | 52.87 | 90.03 | 2 | I |
| 17 | P981007 EX | 25 | 150 | 190.1 | 189.9 | 183.9 | 1 | III |
| 18 | P981007 EP | 25 | 150 | 22.3* | 46.90 | 98.63 | 2 | I |

*Most well-defined mode

These results showed that, at the end of the introduction of ammonia, which corresponds in fact to the end of the exotherm produced by the crystallization of the modafinil, the samples were characterized by:

a high granulometric mode, greater than 170 µm;

a single population; and a single polymorph (III), corresponding to the kinetic form of modafinil.

The samples corresponding to the end product were characterized by:

a much lower granulometric median (<60 µm); and a single polymorph I which in fact corresponds to the thermodynamic form of modafinil.

It was verified, moreover, that the polymorph obtained at the end of the 10 hours of contact with ammonia was indeed identical to that of the end product EP.

Complementary Analyses:

A complementary analysis, to distinguish the particles and the agglomerates present in the samples, was carried out on the powders P981003/EX, P981003/02 (10 h contact) and P981003/PF.

In the sample P981003/EX all the particles are larger than 63 µm. The analysis indicated form III.

For the samples P981003/02 and P981003/PF, two analyses were carried out:

on the fraction smaller than 40 µm (theoretically devoid of agglomerates), and on the fraction larger than 40 µm (theoretically containing a large proportion of agglomerates).

The results showed that two fractions had the same crystalline structure and that there were no agglomerates.

Sample P981004/EX was also assayed for traces of solvents in order to verify if the crystalline form III had come about as the result of the appearance of a solvate or hydrate.

The results observed were as follows:

| | |
|---|---|
| Water content | 0.105% m/m |
| Methanol content | 0.14% m/m |

The low content figures obtained in this analysis allowed the hypothesis of a solvated or hydrated form to be refuted. The polymorph III observed corresponded to a crystalline structure intrinsic to the product alone.

The results obtained at the 100-liter scale provide qualitative confirmation of all the results obtained at the laboratory scale (1 L).

C. 2500-Liter Scale

Example 11

2500-Liter Scale

A reactor of type BE 2500 (De Dietrich) with a capacity of 2500 liters, equipped with an impeller stirrer and a gas introduction pipe, was charged with 250 kg of DMSAM, 750 liters of methanol and 55 liters of water. The suspension was stirred at 100 rpm and 20° C. for 10 min and then heated to 35° C. to dissolve the solids. The solution was subsequently stirred at 100 rpm for 35 min, then cooled to 25° C. and stirred at 100 rpm at this temperature for 30 min.

78 kg of ammonia were then introduced over 4.5 h at 25° C.

The reaction medium was left in contact for 10 h at 25° C. with stirring at 100 rpm before finally being cooled to −10° C., and then was drained and clarified with 40 liters of ice-cold methanol.

The moist product was then dried under vacuum at 45° C.

Yield=89.5%, median=27 µm.

II. Modafinil Synthesis Process without Water

A. 1-Liter Scale

Example 12

1-Liter Scale Procedure

A 1-liter automated reactor of type SIMULAR (Hazard Evaluation Laboratory, HEL) equipped with an impeller stirrer and a gas introduction tube was charged with 240 g of DMSAM and 720 ml of methanol. The suspension was stirred at 200 rpm and 20° C. for 10 min and then heated to 35° C. to dissolve the solids. The solution was subsequently stirred at 200 rpm for 15 min, then cooled to 25° C. and stirred at 350 rpm and at this temperature for 30 min.

50.9 g of ammonia were then introduced over 3 h 10 min at 25° C.

The reaction medium was left in contact for 10 h at 25° C. with stirring at 350 rpm before finally being cooled to −10° C. and then filtered over a frit of porosity 3.

The moist product was then dried under vacuum at 45° C.

Yield=94.9%, median=33.9 µm.

Advantageously it was possible to work with only 3.6 equivalents (and not 4.0) of $NH_3$, added at the same flow rate, while retaining a granulometric median and a granulometric profile which were in accordance with specification.

B. 100-Liter Scale

Example 13

100-Liter Scale Procedure

A reactor of type AE 100 (De Dietrich) with a capacity of 100 liters, equipped with an impeller stirrer (De Dietrich) and a gas introduction pipe, was charged with 24 kg of DMSAM and 72 liters of methanol. The suspension was stirred at 150 rpm and 20° C. for 10 min and then heated to 35° C. to dissolve the solids. The solution was subsequently stirred at 150 rpm for 15 min, then cooled to 25° C. and stirred at 150 rpm at this temperature for 30 min.

5.1 kg of ammonia were then introduced over 3 h 10 min at 25° C.

The reaction medium was left in contact for 10 h at 25° C. with stirring at 150 rpm before finally being cooled to −10° C., and then was drained and clarified with 20 liters of ice-cold methanol.

The moist product was then dried under vacuum at 45° C.

Yield=91.6%, median=34.4 µm.

Example 14

Effect of Stirring Speed

Five experiments were carried out, three of them in accordance with the protocol conditions (stirring speed at 150 rpm; 3.6 eq. $NH_3$ in 3 vol. MeOH).

| | S (rpm) | Median (μm) | Mean (μm) |
|---|---|---|---|
| P010702 EP | 150 | 36.13 | 54.94 |
| P010703 EP | 150 | 34.41 | 57.51 |
| P010706 EP | 175 | 28.49 | 52.79 |
| P010705 EP | 125 | 39.34 | 88.99 |
| P010704 | 150 | 24.55 | 49.23 |

The experiments carried out with the stirring speeds of 125 and 175 rpm showed that the slower stirring speed of 125 rpm results in a granulometric median which, although higher than that obtained at 150 rpm, was nevertheless still in accordance with specification.

Little or no difference, on the other hand, was observed at 175 or 150 rpm.

These experiments satisfied the acceptance criteria, namely:

a yield greater than 90%;
a granulometry: 15/45 μm & polymorph I; and
a DMSAM content of less than 0.3%.

C. 2500-Liter Scale

Example 15

Procedure

A reactor of type BE 2500 (De Dietrich) with a capacity of 2500 liters, equipped with an impeller stirrer and a gas introduction pipe, was charged with 500 kg of DMSAM and 1500 liters of methanol. The suspension was stirred at 100 rpm and 20° C. for 10 min and then heated to 35° C. to dissolve the solids. The solution was subsequently stirred at 100 rpm for 35 min, then cooled to 25° C. and stirred at 100 rpm at this temperature for 30 min.

106 kg of ammonia were then introduced over 3 h 10 min at 25° C.

The reaction medium was left in contact for 10 h at 25° C. with stirring at 100 rpm before finally being cooled to −10° C., and then was drained and clarified with 80 liters of ice-cold methanol.

The moist product was then dried under vacuum at 45° C. Yield=91%, median=23 μm.

The invention claimed is:

1. Process for preparing modafinil having a defined granulometry which comprises the steps of:
    a) preparing a solution of DMSAM in a solvent;
    b) contacting the solution obtained with $NH_3$ at a predetermined temperature and under a predetermined stirring; and
    c) isolating the modafinil formed,
wherein said temperature and said stirring are predetermined in order to obtain modafinil having a granulometry wherein the ratio of median to mean is from 1:3 to 1:0.3 and of median to mode is from 1:3 to 1:0.3.

2. Process according to claim 1, wherein the solvent is a protic polar solvent.

3. Process according to claim 2, wherein the solvent is an alcohol.

4. Process according to claim 3, wherein the solvent is methanol.

5. Process according to claim 4, wherein the solution of DMSAM has a concentration of DMSAM of between 1 and 1.25 mol $L^{-1}$.

6. Process according to claim 1, wherein the temperature in step b) is held between 15 and 65° C.

7. Process according to claim 1, wherein the predetermined stirring speed in step b) is chosen such that the modafinil isolated in step c) has a granulometric median of between 2 and 60 μm.

8. Process according to claim 1, wherein in step b), the solution of DMSAM is contacted with 3 to 6 molar equivalent of $NH_3$.

9. Process according to claim 8, wherein, in step b), the solution of DMSAM is contacted with 3.2 and 5 molar equivalent of $NH_3$.

10. Process according to claim 1, wherein, in step b), the $NH_3$ is introduced into the solution over a sufficient time to obtain a complete dissolution of $NH_3$.

11. Process according to claim 10, wherein in step b), the $NH_3$ is introduced into the solution over a time of between 2 h and 6 h.

12. Process according to claim 11, wherein, in step b), the $NH_3$ is introduced into the solution over a time of between 3 h and 4.5 h.

13. Process according to claim 1, wherein, in step b), the solution is contacted after the introduction of the $NH_3$ for a contact time sufficient to allow the polymorphic transformation of form III to form I.

14. Process according to claim 13, wherein the contact time is between 8 and 12 h.

15. Process according to claim 1, wherein the solution obtained after step b) is further maintained at a temperature lower than the predetermined temperature of step b) for a time sufficient to obtain complete crystallization of modafinil.

16. Process according to claim 15, wherein the solution is further maintained at a temperature lower than the temperature of step b) for a time of from 1 h to 4 h.

17. Process according to claim 15, wherein the temperature is between −20° C. and 0° C.

18. Process according to claim 1, wherein the modafinil isolated in step c) by filtration.

19. Process according to claim 1, wherein the solvent in step a) comprises water.

20. Process according to claim 19, wherein the solvent contains from 5% to 20% by volume of water.

21. Process according to claim 19, wherein the $NH_3$ is introduced into the solution in step b) over a time of between 4 h and 5 h.

22. Process according to claim 19, wherein, in step b), the solution of DMSAM is contacted with 5 to 5.5 molar equivalent of $NH_3$.

23. Process according to claim 1, which does not include a recrystallization step after step c).

24. Process according to claim 1, which does not include a grinding step after step c).

25. Process according to claim 1, wherein the predetermined temperature and stirring speed are chosen such that particles of modafinil form I of which at least:
    50% have a diameter of less than 45 μm, and
    80% have a diameter of less than 110 μm, and
    95% have a diameter of less than 220 μm, are isolated in step c).

26. Process according to claim 1, wherein the modafinil isolated in step c) is modafinil form III.

27. Process according to claim 1, wherein the modafinil isolated in step c) is modafinil form I.

28. Process according to claim 1, wherein modafinil with a granulometric median of between 1 μm and 1 mm is isolated in step c).

29. Process according to claim 1, wherein the levorotary enantiomer of DMSAM is employed in step a).

30. Process according to claim 1, wherein the dextrorotary enantiomer of DMSAM is employed in step a).

31. Process according to claim 7, wherein the predetermined stirring speed in step b) is chosen such that the modafinil isolated in step c) has a granulometric median of between 15 and 45 μm.

* * * * *

UNITED STATES PATENT AND TRADEMARK OFFICE
CERTIFICATE OF CORRECTION

| | | |
|---|---|---|
| PATENT NO. | : 7,541,493 B2 | Page 1 of 1 |
| APPLICATION NO. | : 10/557072 | |
| DATED | : June 2, 2009 | |
| INVENTOR(S) | : Rose | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 422 days Delete the phrase "by 422 days" and insert -- by 576 days --

Signed and Sealed this

Third Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,541,493 B2 | Page 1 of 1 |
| APPLICATION NO. | : 10/557072 | |
| DATED | : June 2, 2009 | |
| INVENTOR(S) | : S. Rose | |

It is certified that error appears in the above-identified patent and that said Letters Patent is hereby corrected as shown below:

In column 18, claim 9, line 10, please replace the word "and" with --to--.

Signed and Sealed this
Eighth Day of March, 2011

David J. Kappos
*Director of the United States Patent and Trademark Office*